(12) United States Patent
Tiberi et al.

(10) Patent No.: US 10,349,863 B2
(45) Date of Patent: Jul. 16, 2019

(54) APPARATUS FOR TESTING THE INTEGRITY OF MAMMARY TISSUES

(71) Applicant: UBT S.r.l., Assisi (Perugia) (IT)

(72) Inventors: Gianluigi Tiberi, Montefalco (IT); Giovanni Raspa, Rivotorto di Assisi (IT)

(73) Assignee: UBT S.R.L, Assisi (Perugia) (IT)

( * ) Notice: Subject to any disclaimer, the term of this patent is extended or adjusted under 35 U.S.C. 154(b) by 1124 days.

(21) Appl. No.: 14/429,032

(22) PCT Filed: Sep. 16, 2013

(86) PCT No.: PCT/IB2013/058573
§ 371 (c)(1),
(2) Date: Mar. 18, 2015

(87) PCT Pub. No.: WO2014/045181
PCT Pub. Date: Mar. 27, 2014

(65) Prior Publication Data
US 2015/0230725 A1    Aug. 20, 2015

(30) Foreign Application Priority Data
Sep. 18, 2012 (IT) .............................. MI2012A1542

(51) Int. Cl.
*A61B 5/00* (2006.01)
*A61B 5/05* (2006.01)

(52) U.S. Cl.
CPC .......... *A61B 5/0507* (2013.01); *A61B 5/4312* (2013.01); *A61B 5/708* (2013.01)

(58) Field of Classification Search
CPC ...... A61B 5/0507; A61B 5/4312; A61B 5/708
See application file for complete search history.

(56) References Cited

U.S. PATENT DOCUMENTS

| 4,831,384 A | * | 5/1989 | Sefton, Jr. | .............. H01Q 15/24 342/188 |
| 2004/0077943 A1 | * | 4/2004 | Meaney | .................. A61B 5/05 600/430 |
| 2005/0143638 A1 | * | 6/2005 | Johnson | ............... A61B 5/4312 600/407 |

OTHER PUBLICATIONS

International Search Report and Written Opinion dated Jan. 29, 2014 for corresponding international patent application No. PCT/IB2013/058573.

(Continued)

*Primary Examiner* — Rajeev P Siripurapu
(74) *Attorney, Agent, or Firm* — Workman Nydegger

(57) ABSTRACT

The disclosure describes an apparatus for testing the integrity of mammary tissues comprising one or more transmission antennas configured to strike a mammary tissue with a main electromagnetic field in the microwave frequency band, one or more reception antennas configured to pick up a corresponding reflected electromagnetic field, a processing unit comprising a first operating module configured to determine a main parameter representing an electrical discontinuity of the mammary tissue, and a second operating module configured to generate a signal representing a non-integrity of the mammary tissue.

11 Claims, 4 Drawing Sheets

(56) References Cited

OTHER PUBLICATIONS

Navid Ghavami et al.; "UWB Microwave Imaging of Objects with Canonical Shape"; IEEE Transactions on Antennas and Propagation, vol. 6, No. 1; Jan. 2012.
Grzegorczyk T M et al.; "Fast 3-D Tomographic Microwave Imaging for Breast Cancer Detection"; IEEE Transactions on Medical Imaging, vol. 31, No. 8; Aug. 2012.

\* cited by examiner

APPARATUS FOR TESTING THE INTEGRITY OF MAMMARY TISSUES

BACKGROUND

Technical Field

The present disclosure relates to an apparatus for testing the integrity of mammary tissues.

In particular, the disclosure relates to an apparatus which allows the detection of breast tumours and the test by means of imaging of the integrity of portions of the body.

Description of the Related Art

As it is well known, in medical applications methods of analysis based on imaging are considered of great interest.

The known methods provide tomographic reconstructions of tissues using different means:
ultrasound scanners;
X-ray based computed tomography (CT);
nuclear magnetic resonance imaging (MRI)
Such methods are affected by multiple problems.
ultrasound is subject to problems of contrast and inability to detect images of objects with high differences in terms of acoustic impedance, such as in areas with air and bone;
tomography entails administering doses of ionizing radiation to the patient;
magnetic resonance requires lengthy periods of application of the magnetic field and is very costly.

Moreover, in the specific application of breast cancer detection, the limitations of X-ray mammography are well known.

More precisely, this technique, even with high-resolution images and with relatively low doses of radiation, fails to detect approximately 15% of cancers present, while approximately 75% of the identified breast lesions are, really, benign.

Over time, microwave imaging has attracted increasing attention, especially for its applicability in breast cancer detection; this is due to the significant contrast that is detected between normal and malign tissues, characteristic of the dielectric properties of the tissues at microwave frequencies.

Current research in microwave breast imaging can be divided into:
microwave tomography;
ultra-wide band (UWB) radio techniques.

Unfortunately, these methods, too, are affected by multiple problems:
tomography is intrinsically unstable, since it requires solving a nonlinear inverse problem;
in UWB, complex focusing techniques are necessary; in some cases filters are necessary to improve the suppression of possible disturbing images (clutter suppression) and the spatial discrimination, but these entail an increase in complexity;
approaches based on time reversal (TR) techniques have also been proposed, but they require knowledge of the channel transfer function associated with the feedback.

It should also be underlined that the proposed methods are characterized by a low S/C ratio.

In the literature of imaging analysis for breast cancer performed at microwave frequencies, the S/C ratio (Signal-to-Clutter ratio) within the breast area is assumed to be the ratio between the maximum response identifying a tumour and the maximum response identifying a possible image of disturbance (clutter) in the same image.

It may be deduced that the higher this ratio is, the better is the detection and determination of the position of possible non-integrities in the mammary tissue.

By way of example, in the previously mentioned technique which exploits focusing algorithms, the S/C ratio detected within the mammary tissue is 4 dB.

US patent application having publication number US 2006/0241409 discloses a microwave system for estimating the average dielectric properties of a breast tissue, in order to detect the presence and location of a tumour. This is achieved using an iterative method which is an extension of the time-domain inverse scattering algorithm based on a finite-difference time-domain method.

US patent application having publication number US 2011/0130656 discloses a microwave image reconstruction apparatus for the diagnosis of breast cancer. The apparatus comprises a plurality of antennas 190 1, #2, ... #16 arranged in such a way as to permit insertion of a breast (see FIG. 2). The breast image reconstruction uses an iterative algorithm which comprises a log transformation of the amplitude values of the electromagnetic wave received from the plurality of antennas 190 1, #2, ... #16, in order to improve the sensitivity and to reduce the number of performed calculations.

BRIEF SUMMARY

In light of the above, one embodiment of the present disclosure is an apparatus for testing the integrity of mammary tissues which allows the integrity of such tissues to be identified in a precise and reliable manner.

Another embodiment of the disclosure is an apparatus which allows both to determine the presence of a non-integrity in mammary tissue, and to locate the same with precision within the mammary tissue.

These and other objects are achieved by an apparatus for testing the integrity of mammary tissues according to what is disclosed in the appended claims.

The apparatus, as disclosed, achieves the following technical effects:
it allows a precise and reliable identification of the integrity of mammary tissues;
it allows to determine the presence of a non-integrity and to locate the same with precision within the mammary tissue;
it allows to determine, in a non-invasive and simultaneously reliable manner, the presence of non-integrity in a mammary tissue.
it is of simple construction and implementation.

The aforesaid technical effects and other technical effects of the disclosure will be apparent in greater detail from the description that follows of an exemplary embodiment, given by way of illustration and not by way of limitation with reference to the appended drawings.

DETAILED DESCRIPTION

Figure 1:
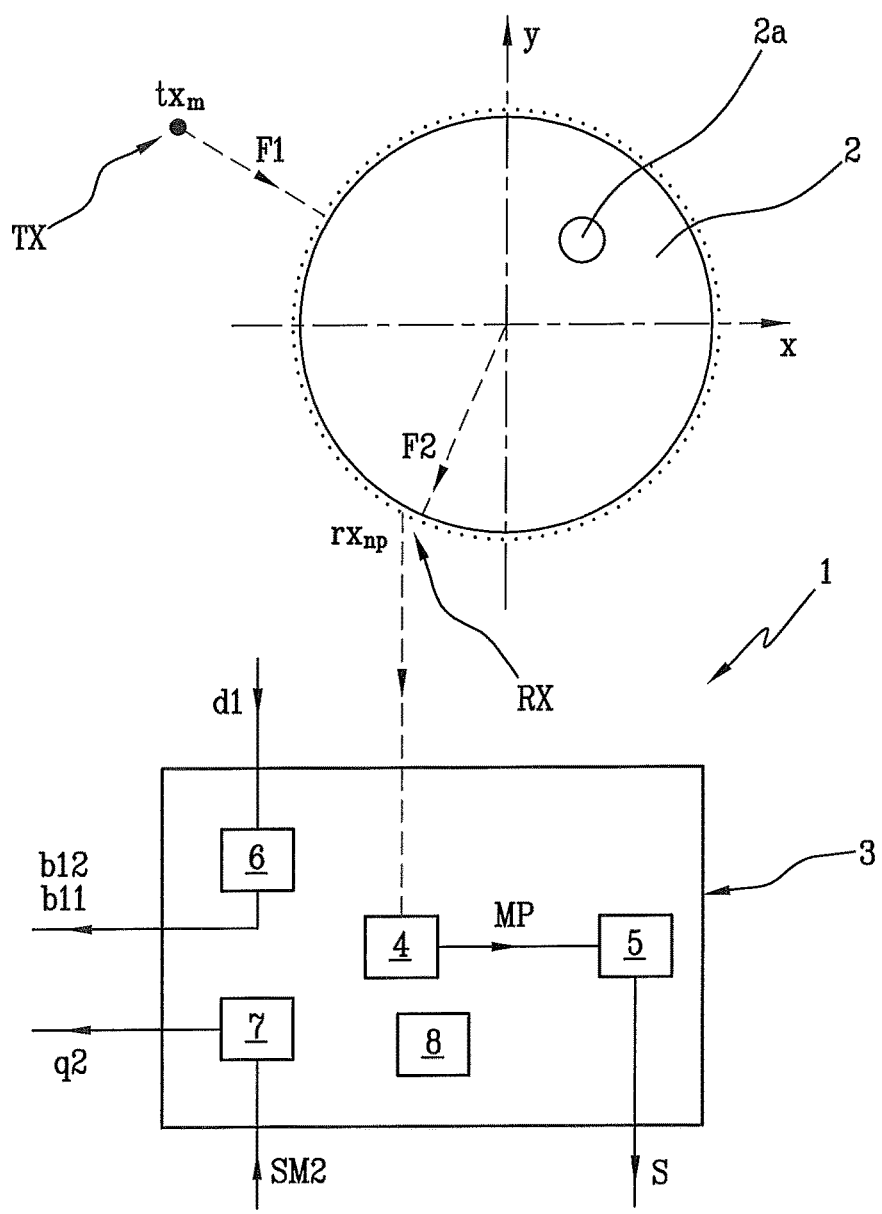
FIG. 1 shows a block diagram representing the disclosure.
Figure 2A:
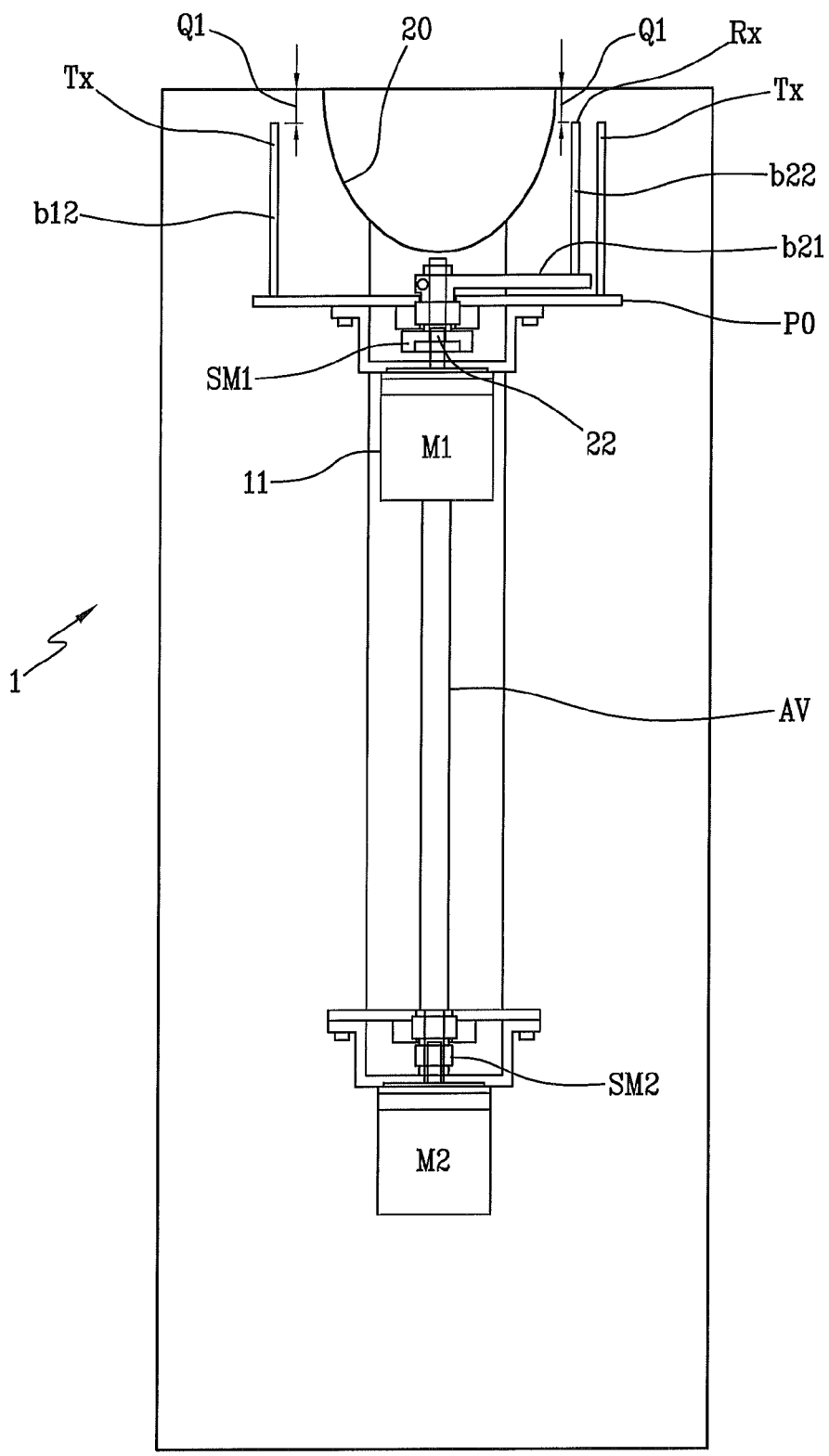
FIGS. 2a, 2b and 2c show a schematic view of the apparatus of the disclosure.
Figure 2B:
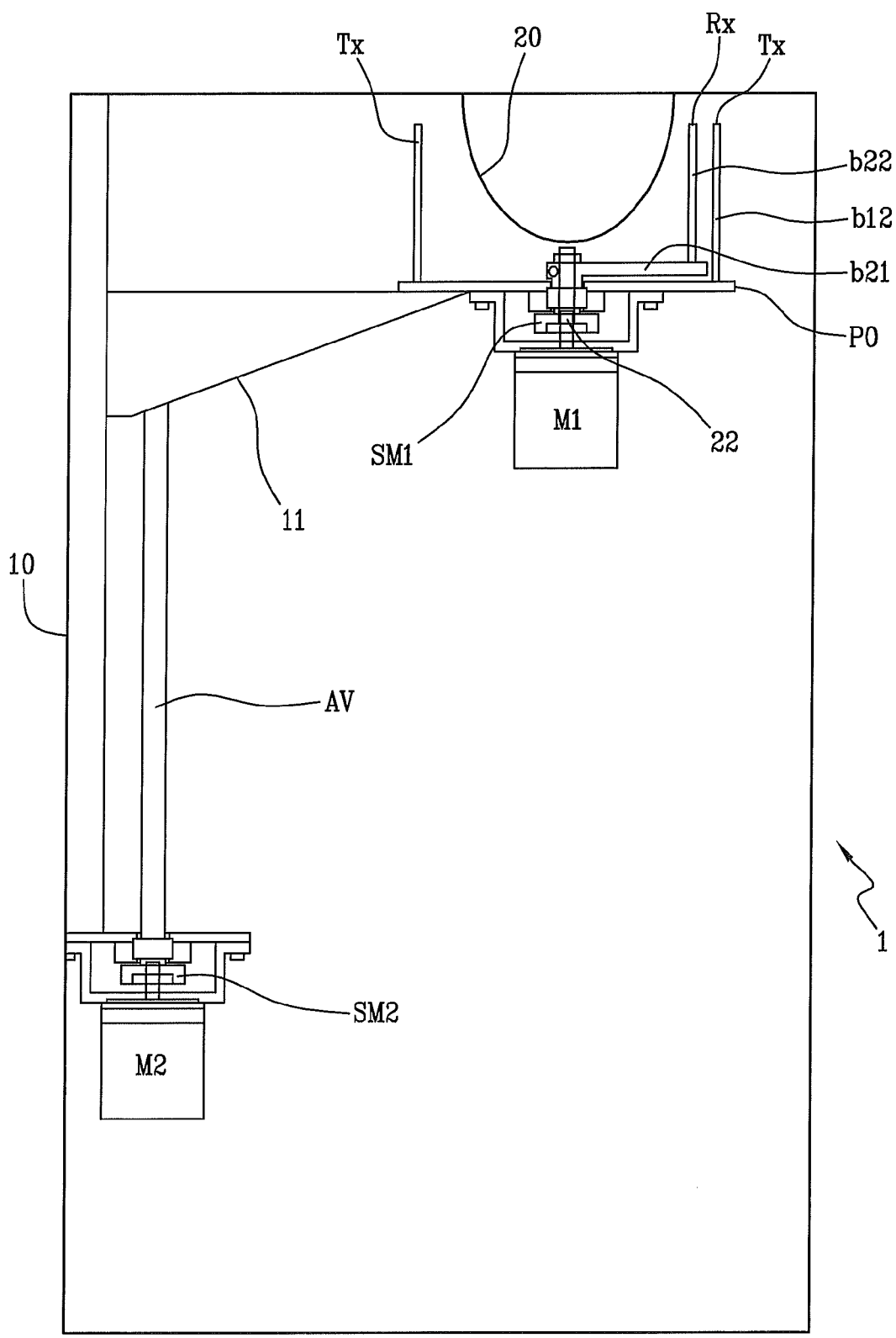
Figure 2C:
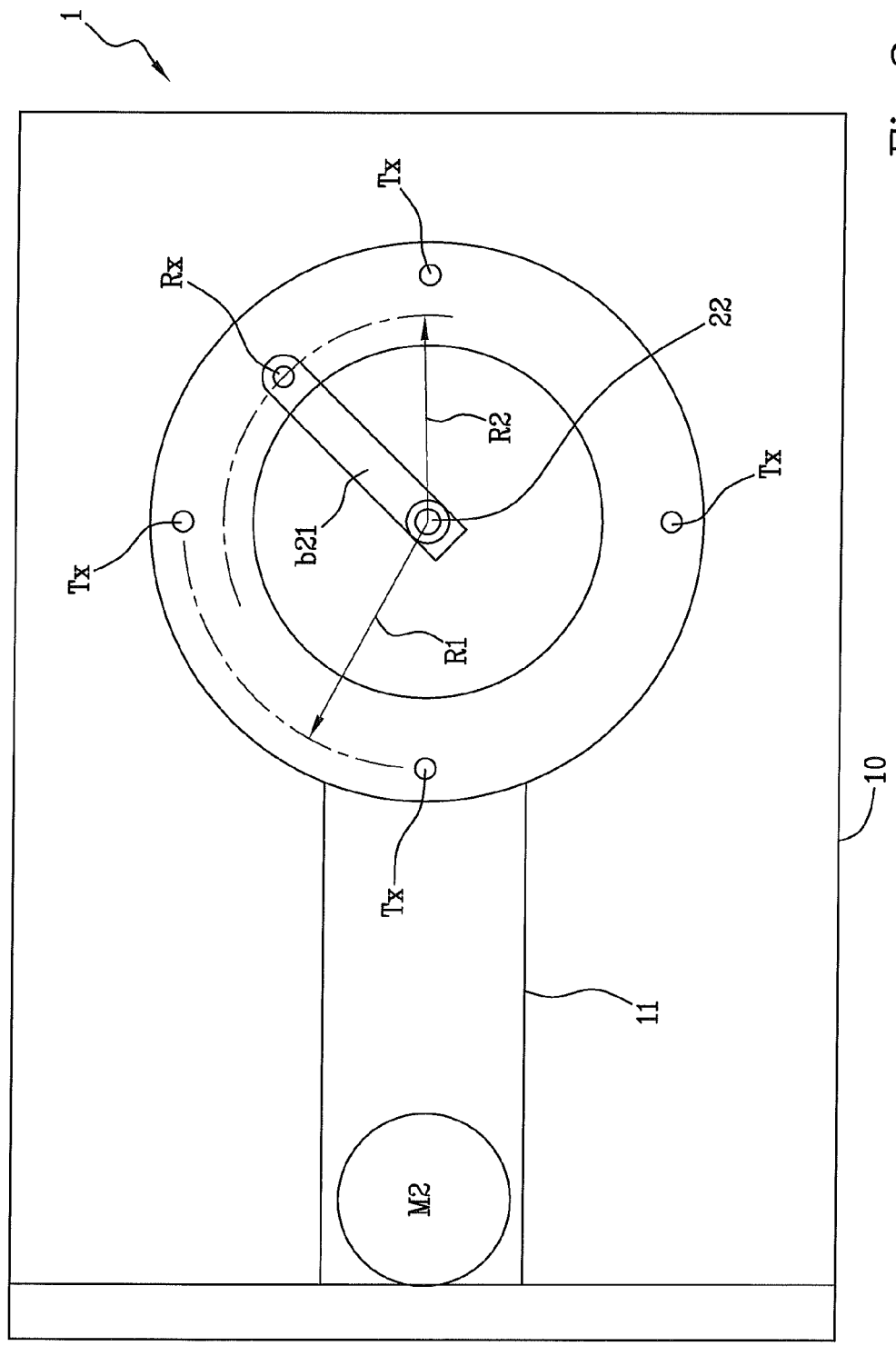

The disclosure relates to an apparatus for testing the integrity of mammary tissues comprising one or more antennas transmitting towards the mammary tissue and operating in the microwave band, one or more antennas receiving from the mammary tissue and operating in the microwave band, and a processing unit configured to determine a main parameter representing an electrical discontinuity of the mammary tissue and to generate a signal representing a non-integrity of the mammary tissue.

With reference to the figures, 1 indicates overall an apparatus for testing the integrity of mammary tissues according to the present disclosure.

In the present description and in the subsequent claims, the term "mammary tissue" will mean the tissue comprising a glandular component, an adipose component, in which the glandular structures are inserted and immersed, and a fibrous supporting component, which generates subdivisions among the various glandular appendages.

By way of example, the mammary tissue 2 can display a relative dielectric constant in the range of 1 to 20.

By way of example, the mammary tissue 2 can have a conductivity comprised between 0 S/m and 1 S/m.

The apparatus according to the disclosure, as will be clearer hereinafter, is configured to determine the presence of non-integrity within the mammary tissue 2 based on possible discontinuities in the electrical behaviour of the mammary tissue itself.

In the course of the description, the term "non-integrity" will mean an inhomogeneity in the mammary tissue indicative of anomalous conditions in the composition of the tissue itself.

In practical terms, the disclosure allows to identify, within the mass of mammary tissue 2 (assumed to be homogeneous, within certain limits), areas in which the relative dielectric constant and/or the conductivity have significant variations (for example, an increase of at least 25%).

In particular, the relative dielectric constant and the conductivity of the mammary tissue are known beforehand, even if in a manner that is not wholly precise.

With reference to the figures, the apparatus for testing the integrity of mammary tissues 1 comprises a fixed supporting structure or casing 10 on which a movable frame structure 11 is mounted.

The movable frame structure 11 comprises a substantially horizontal platform PO.

The apparatus according to the disclosure comprises a first motor M1 associated with the horizontal platform PO.

In particular, the first motor M1 is coupled to a hub 22 passing through the horizontal platform PO.

The fixed supporting structure 10 is configured to comprise the motor M1 and the electromagnetic transceiver components described below.

In particular, the fixed supporting structure 10 is configured substantially as a parallelepiped.

The top part of 10 comprises a cup-shaped recess 20 configured to support the mammary tissue 2 to be analyzed.

The apparatus 1 of the disclosure further comprises a vertical axis AV which is substantially perpendicular to the platform PO.

According to the disclosure, the vertical axis AV is associated with a second motor M2 configured to slide a carriage associated with the first platform PO along the axis AV.

In other words, the positioning of the horizontal platform PO at a predefined height for measuring the mammary tissue is determined by the motor M2.

The motor M2 rotates a ball screw on which a carriage connected to the horizontal platform slides.

Alternatively, the positioning of the horizontal platform PO on the vertical axis can be achieved with equivalent mechanical means such as belts, racks, chains etc.

The initial height position is indicated to the test system by means of a sensor SM2.

With reference to the figures, the apparatus for testing the integrity of a mammary tissue according to the disclosure comprises one or more transmission antennas TX.

These antennas are configured to strike a mammary tissue 2 with a main electromagnetic field F1.

The antennas Tx are mounted inside the casing 10.

The antennas Tx are concentric to the hub 22 and can be mounted on the platform PO.

In particular, the main electromagnetic field F1 is defined in a band in the microwave frequency interval.

In particular, the frequencies can be comprised between 0.5 GHz and 4 GHz, more in particular between 1 GHz and 3 GHz.

In particular, the mammary tissue 2 is struck by a plurality of electromagnetic fields coming from different directions.

In the preferred embodiment, the use of one or more transmission antennas TX is envisaged.

In particular, a plurality of transmission antennas TX can be used for the purpose of generating the aforesaid electromagnetic fields coming from different directions.

In other words, the transmission antennas TX are configured to generate the main electromagnetic field F1 originating from different positions.

In one embodiment, use can be made of a single transmission antenna TX, suitably moved in relation to the mammary tissue 2 so as to assume different positions over time and thus strike the mammary tissue 2 with electromagnetic fields coming from different directions.

It is likewise envisaged that several transmission antennas TX can be moved in relation to the mammary tissue 2.

In one embodiment, the transmission antennas TX can both be moved in relation to the mammary tissue 2, and switched (i.e. driven between on/off conditions) in such a way as to generate the desired electromagnetic fields in the planned directions and time intervals.

In particular, the mammary tissue 2 has a conformation with substantially circular sections.

In one embodiment, the transmission antennas TX are positioned around the mammary tissue 2, in particular at a given height Q1 relative to the base of the mammary tissue to be analyzed.

In other words, the antennas Tx are mounted on first supports b12 projecting from the platform PO.

The transmission antennas TX can be set at a height Q1 defined according to the mammary tissue to be measured.

The transmission antennas TX can be distributed around the mammary tissue 2 over a circumference with a radius R1.

In one embodiment the circumferential distribution of the transmission antennas TX, relative to the mammary tissue 2, can be substantially angularly uniform.

In particular, there are at least three transmission antennas TX, so as to allow to eliminate the so-called transmitter "image" and prevent the latter from undermining the quality of the measurement.

With reference to the figures, the apparatus for testing the integrity of a mammary tissue according to the disclosure comprises one or more reception antennas RX configured to pick up a reflected electromagnetic field F2 corresponding to the transmitted field F1.

These antennas Rx are mounted inside the casing 12.

The antennas Rx are rotatably associated with the hub 22 by means of arms b21.

In other words, the arms b21 rotating around the hub 22 bring about a rotation of the antennas RX in a circular pattern with a radius R2.

The measurement can take place using one or more reception antennas RX. In one embodiment, use can be made of a single reception antenna RX, suitably moved so as to assume different positions over time around the mammary tissue 2.

It is likewise envisaged that a greater number of reception antennas RX can be moved in relation to the mammary tissue 2.

As for the transmission antennas, in one embodiment the reception antennas RX can be positioned at a given height Q1.

In other words, the antennas Rx are mounted on second supports b22 projecting from the arms b21.

In the case of the reception antennas RX as well, the height Q1 is defined as a function of the mammary tissue to be measured.

In particular, the reception antennas RX and transmission antennas TX are positioned at the same height Q1.

In particular, the antennas Tx and Rx are both positioned substantially at a height Q1 equal to half the height of the mammary tissue 2.

Conveniently, the transmission antennas TX are arranged in a more radially external position than the reception antennas RX, relative to the mammary tissue 2. This position of the antennas is optimal for applying Huygens' principle to calculate the electromagnetic field within the mammary tissue 2, which will be explained below. In fact, said position of the antennas ensures the possibility of measuring the electromagnetic field on a closed external surface substantially in contact with the mammary tissue 2 to be analyzed.

In practical terms, the transmission antennas TX are positioned at a greater distance from the mammary tissue 2, i.e. at the distance R1, than the reception antennas RX, which are at a distance R2.

In particular, the transmission antennas TX are at a certain distance from the object, whereas the reception antennas are in the immediate proximity of (nearly in contact with) the mammary tissue 2 and positioned on a rotating support with, for example, an angular resolution of nine degrees.

The dimension of the arm b21 determines the respective radius R2. In one embodiment, it can also be assumed to be variable as a function of the dimensions of the mammary tissue 2 to be measured.

The electrical connection between the rotating antenna Rx and the receiving device is ensured by means of a coaxial rotary joint.

As an alternative to the rotary joint, the connection can be made by means of a flexible spiral cable and with reversal movements of the direction of rotation every 360 degrees.

The zero starting point of rotation is indicated to the control system by means of a sensor SM1.

In particular, four transmitting antennas Tx1, Tx2, Tx3, Tx4 are fixed to the horizontal platform Po, at a distance equal to the radius R1 greater than R2.

In a preferred embodiment, the number of antennas Tx is 3.

In other embodiments, this number can be greater than or equal to 4.

The antennas (four in this case) are positioned on circumferential arcs equal to 90 degrees with a radius R1, and are connected to the receiving device by means of a coaxial switch which determines the activation sequence thereof. In one variant, as a replacement for the fixed antennas TX, it is possible to put a single antenna TX which is positioned by a motor M3, not shown in the figure, and is coupled with or replaces the first motor M1, in the circumferential arc established by the measuring sequence.

In particular, the motor M3 is coupled with a hub 21 (not shown in the figure) which is concentric to the hub 22 and passes through the horizontal platform PO.

The antenna TX is rotatably associated with the hub 21 by means of the arm b11.

The system for positioning the antenna TX pivots on the hub 21 which is concentric to the hub 22 of the antenna Rx.

The zero starting point of rotation is indicated to the control system by means of a sensor SM3.

In particular, the transmission and reception antennas are isolated from the remaining part of the structure by means of a coating made of microwave absorbing material.

With particular reference to FIG. 1, the apparatus for testing the integrity of a mammary tissue comprises a processing unit 3 configured to process parameters representing the electromagnetic fields F1 and F2.

In general it should be noted that in the present context and in the subsequent claims, the processing unit 3 is presented as divided into distinct functional modules (memory modules or operating modules) solely for the purpose of describing the functions of the unit itself in a clear and complete manner.

In reality, the processing unit 3 can consist of a single electronic device (e.g. a PC, a notebook, or the like), duly programmed to carry out the described functions, and the different modules can correspond to hardware entities and/or to routine software belonging to the programmed device.

Alternatively, or in addition, the functions can be performed by a plurality of electronic devices over which the aforesaid functional modules can be distributed.

The processing unit 3 can moreover rely on one or more processors to execute the instructions contained in the memory modules.

Furthermore, the aforesaid functional modules can be distributed over different local or remote computers based on the architecture of the network they are connected to.

According to the disclosure, the processing unit 3 comprises a first operating module 4 configured to determine, as a function of the reflected electromagnetic field F2, a main parameter MP representing an electrical discontinuity of the mammary tissue 2.

As a function of the main parameter MP, it is thus possible to establish whether there is a non-integrity within the mammary tissue 2.

In other words, as a function of the main parameter MP it is possible to establish whether there is an anomaly in the composition of the mammary tissue 2.

In still other words, based on the main parameter MP, it is possible to establish whether there is an inhomogeneity in the mammary tissue 2.

According to the disclosure, the processing unit 3 comprises a second operating module 5 configured to generate, as a function of the main parameter MP, a signal S representing a non-integrity 2a of the mammary tissue 2.

The signal S can be generated by the operating module 5, for example, and will output (for example via a screen or monitor) a value representing the mere presence, or also the position, of the non-integrity of the mammary tissue 2.

In one embodiment, by exploiting the technical features of the disclosure it is also possible to determine the position of the non-integrity within the mammary tissue 2.

With the procedure of the disclosure, the value of the S/C ratio within the mammary tissue is approximately 8 dB, i.e. about double the value obtained with the technique that exploits focusing algorithms.

Going into further detail, the disclosure is based on the following considerations.

Let us consider a mammary tissue 2 having substantially circular sections; let us assume that the radius of the section corresponding to the height Q1 is $a_0$. The value of $a_0$ can vary between 2 and 10 cm.

The mammary tissue 2 is illuminated by at least one antenna tx operating in the given frequency band.

It is assumed that we know the dielectric constant and conductivity of the mammary tissue 2 beforehand; this information does not necessarily have to be particularly accurate.

It is assumed, moreover, that if the mammary tissue 2 displays homogeneous behaviour in terms of dielectric constant and conductivity, it can be considered intact, i.e. free of detectable pathologies.

In contrast, if discontinuities were to be found, the assessment as to integrity would change and cases could occur in which anomalies are present.

Let us suppose that the field transmitted by Tx is measured in the points $rx_{np} \equiv (a_0, \varphi_{np})$ with np=1, ..., NPT located on the surface. In greater detail, the transfer function is measured in modulus and phase via a VNA or equivalent architecture, also called s12. The transfer function is measured in the operating band over a number NF of discrete frequencies $f_i$. Exploiting Huygens' principle, the field within the mammary tissue 2 is calculated. In particular, the first operating module 4 is further configured to calculate, as a function of the reflected electromagnetic field F2 and exploiting Huygens' principle, an electromagnetic field within the mammary tissue 2 and is further configured to determine, as a function of the electromagnetic field calculated within the mammary tissue, the main parameter MP representing the electrical discontinuity of the mammary tissue 2. The use of Huygens' principle ensures a higher signal-to-clutter ratio as compared to the known techniques and a better resolution, other parameters being equal. Moreover, the application of Huygens' principle does not require the use of iterative algorithms and is thus numerically more stable. Finally, the use of Huygens' principle does not require synchronization between the transmission antennas TX and reception antennas RX: as a result, the apparatus 1 is simpler and more cheap to make.

If the mammary tissue 2 contains a non-integrity, the image I will show a peak signal in the site corresponding to the position of the non-integrity itself. In particular, the peak is characterized by an S/C ratio of around 8 dB, obtained using a band comprised between 1 GHz and 3 GHz, and at least three transmission antennas TX.

In order to remove possible artifacts, time-domain filtering can be used in an appropriate manner.

Going into greater detail, the following steps can be carried out:

one starts from the transfer function in the frequency domain; said signal could contain contributions reflected/scattered by the environment wherein the measurement is performed, which are thus "external" to the mammary tissue being analyzed;

one passes into the time domain via an inverse Fourier transform; possible "external" contributions (i.e. reflected/scattered by the environment where the measurement is performed) will show themselves with a greater delay than the "internal" contributions (i.e. reflected/scattered by the mammary tissue being analyzed);

the time-domain signal is multiplied by a time window in order to filter out the "external" components;

one returns to the frequency domain via a Fourier transform.

The transfer function can be obtained at NF=625 discrete frequencies between 1 GHz and 3 GHz.

The field can be measured in $N_{pt}$=40 angularly equidistant points on the surface of the mammary tissue 2.

A total of M=4 data series (m=1 ... 4) are obtained by varying the position of the transmission antenna by steps of 90°.

In one embodiment, the frequency band, NF, $N_{pt}$, M can be varied.

In order to perform a 3D imaging operation, the procedure disclosed and claimed can be repeated a number of times, positioning the antennas at different heights along the height, i.e. the longitudinal extent, of the mammary tissue. In this way it is be possible to obtain a three-dimensional image of the non-integrity 2a of the mammary tissue 2, thus enabling the spatial extent of the anomalous condition of the composition of the mammary tissue 2 to be observed and thus improving the ability to quantify the anomalous condition itself.

The processing unit 3 can further comprise a positioning module 6.

The positioning module 6 is configured to determine the dimensions of the arms 21 as a function of the mammary tissue to be measured.

In other words, the apparatus of the disclosure can comprise a sensor S4 positioned in proximity to the cup 20 and configured to measure the dimensions dl of the mammary tissue 2.

The positioning module 6 receives the value of the dimensions dl as input and determines a corresponding variation of the arms b21.

The processing unit 3 further comprises a second positioning module 7.

The second positioning module 7 is configured to move the supporting platform PO along the vertical axis AV.

In other words, the second positioning module 7 is configured to drive the second motor M2 to position the horizontal platform PO at a predefined height Q1 for measuring the mammary tissue.

The initial height is indicated to the control system by means of the previously described sensor SM2.

The processing unit 3 according to the disclosure further comprises a control module 8.

The control module 8 is configured to control one or more transmission antennas (TX) and/or one or more reception antennas (RX) so as to switch them between an activation condition and a deactivation condition.

The technical effect achieved is an optimal measurement of the mammary tissue 2 to be tested.

The disclosure achieves important advantages.

Firstly, the apparatus according to the disclosure makes it possible to determine, in a non-invasive and simultaneously reliable manner, the presence of non-integrity in a mammary tissue 2.

Furthermore, in a non-invasive manner and at the same time with a high degree of reliability, the apparatus according to the disclosure makes it possible to determine the position of the non-integrity within the mammary tissue 2.

Additionally, the apparatus allows an optimal positioning of the electromagnetic transceiving antennas so as to ensure an optimal test of the mammary tissue.

The invention claimed is:

1. An apparatus for testing an integrity of a mammary tissue, the apparatus comprising:
   a platform;
   one or more transmission antennas operating in a band of microwaves configured to strike a mammary tissue with a main electromagnetic field;
   one or more reception antennas operating in the band of microwaves and configured to pick up a corresponding reflected electromagnetic field;
   a processor configured to:
      determine, as a function of said reflected electromagnetic field, a main parameter representing an electrical discontinuity of said mammary tissue; and
      generate, as a function of said main parameter, a signal representing a non-integrity of said mammary tissue;
   wherein said one or more transmission antennas are arranged in a more radially external position than said one or more reception antennas, with respect to said mammary tissue;
   a hub;
   at least one arm to rotatably associate the one or more reception antennas to the hub;
   a coaxial rotary joint for electrically connecting the one or more reception antennas to the processor as the one or more reception antennas rotate, wherein the one or more reception antennas are configured to be rotatably moved, in such a way as to pick up said reflected electromagnetic field in different directions; and
   a motor for positioning the platform at a predefined height such that said or more transmission antennas and said one or more reception antennas are repeatedly positioned at different heights along a height of the mammary tissue.

2. The apparatus according to claim 1, wherein the processor is further configured to:
   calculate, as a function of said reflected electromagnetic field and exploiting the Huygens' principle, an electromagnetic field within the mammary tissue;
   determine, as a function of the electromagnetic field calculated within the mammary tissue, said main parameter representing the electrical discontinuity of the mammary tissue.

3. The apparatus according to claim 1, wherein said one or more transmission antennas are configured to generate said main electromagnetic field originating from different positions.

4. The apparatus according to claim 3, wherein said one or more transmission antennas are each positioned in a respective position, for the emission of said main electromagnetic field.

5. The apparatus according to claim 4, wherein the one or more transmission antennas are configured to emit said radiation in a predetermined frequency interval.

6. The apparatus according to claim 3, wherein said one or more transmission antennas are positioned in at least three different positions.

7. The apparatus according to claim 1, wherein said processor is further configured to control one or more of said one or more transmission antennas and/or one or more of said one or more reception antennas so as to switch them between an activation condition and a deactivation condition.

8. The apparatus according to claim 1, further comprising:
   a fixed supporting structure;
   a movable frame structure mounted on the fixed supporting structure;
   wherein the movable frame structure comprises a substantially horizontal platform,
   wherein the hub passes through the horizontal platform.

9. The apparatus according to claim 8, wherein:
   the one or more transmission antennas are mounted on first supports projecting from the platform,
   the at least one arm comprises a support projecting from the arm, with the one or more reception antennas being mounted on said support, wherein the arm is adapted to rotate around the hub to bring about a rotation of the one or more reception antennas, and
   the platform is arranged horizontally,
   further comprising:
   a motor coupled to the hub.

10. The apparatus according to claim 1, wherein the at least one transmission antennas and the one or more reception antennas are isolated from the remaining part of the structure by means of a coating of microwave absorbing material.

11. An apparatus for testing an integrity of a mammary tissue, the apparatus comprising:
   a fixed supporting structure and a movable frame structure mounted thereon, the movable frame structure comprising a substantially horizontal platform;
   one or more transmission antennas mounted on the platform and operating in a band of microwaves configured to strike a mammary tissue with a main electromagnetic field;
   one or more reception antennas operating in the band of microwaves and configured to pick up a corresponding reflected electromagnetic field;
   a processor configured to:
      determine, as a function of said reflected electromagnetic field, a main parameter representing an electrical discontinuity of said mammary tissue;
      generate, as a function of said main parameter, a signal representing a non-integrity of said mammary tissue;
   wherein said one or more transmission antennas are mounted on first supports projecting from the platform;
   a hub passing through the platform;
   a motor coupled to the hub;
   at least one arm comprising a support projecting from the arm, with the one or more reception antennas being mounted on said support, wherein the at least one arm is adapted to rotate around the hub to bring about a rotation of the one or more reception antennas,
   wherein said one or more transmission antennas are arranged in a more radially external position than said one or more reception antennas, with respect to said mammary tissue,
   wherein said one or more reception antennas are configured to be rotatably moved, in such a way as to pick up said reflected electromagnetic field in different directions,
   a coaxial rotary joint for electrically connecting the one or more rotating reception antennas to the processor;
   a motor for positioning of the horizontal platform at a predefined height, such that said one or more transmission antennas and said one or more reception antennas are repeatedly positioned at different heights along the height of the mammary tissue.

* * * * *